(12) United States Patent
Pearlman et al.

(10) Patent No.: US 11,944,426 B2
(45) Date of Patent: Apr. 2, 2024

(54) AXIAL LOAD CELL

(71) Applicants: UNIVERSITY OF PITTSBURGH—OF THE COMMONWEALTH SYSTEM OF HIGHER EDUCATION, Pittsburgh, PA (US); THE UNITED STATES GOVERNMENT AS REPRESENTED BY THE DEPARTMENT OF VETERANS AFFAIRS, Washington, DC (US)

(72) Inventors: Jonathan L. Pearlman, Pittsburgh, PA (US); Jonathan A. Duvall, Pittsburgh, PA (US); Samuel T. Bucior, Greenboro, NC (US)

(73) Assignees: University of Pittsburgh-Of the Commonwealth System of Higher Education, Pittsburgh, PA (US); The United States Government as Represented by the Department of Veterans Affairs, Washington, DC (US)

( * ) Notice: Subject to any disclaimer, the term of this patent is extended or adjusted under 35 U.S.C. 154(b) by 933 days.

(21) Appl. No.: 16/959,589

(22) PCT Filed: Jan. 11, 2019

(86) PCT No.: PCT/US2019/013129
§ 371 (c)(1),
(2) Date: Jul. 1, 2020

(87) PCT Pub. No.: WO2019/140148
PCT Pub. Date: Jul. 18, 2019

(65) Prior Publication Data
US 2021/0128019 A1    May 6, 2021

Related U.S. Application Data

(60) Provisional application No. 62/616,619, filed on Jan. 12, 2018.

(51) Int. Cl.
A61B 5/103 (2006.01)
A61B 5/00 (2006.01)
(Continued)

(52) U.S. Cl.
CPC .......... *A61B 5/1036* (2013.01); *A61B 5/6891* (2013.01); *A61B 5/6894* (2013.01);
(Continued)

(58) Field of Classification Search
CPC ... A61B 5/1036; A61B 5/6891; A61B 5/6894; A61B 2503/00; A61B 2562/0252;
(Continued)

(56) References Cited

U.S. PATENT DOCUMENTS 3,988,934 A    11/1976    Kamphoefner et al.
4,162,628 A    7/1979    Oetjen et al.
(Continued)

FOREIGN PATENT DOCUMENTS

GB    2147426 A    5/1985
WO    2016118546 A1    7/2016
(Continued)

OTHER PUBLICATIONS

Jentoft, L. P., Dollar, A. M., Wagner, C. R., & Howe, R. D. (2014). Intrinsic Embedded Sensors for Polymeric Mechatronics: Flexure and Force Sensing. Sensors (Basel, Switzerland), 14(3), 3861-3870. http://doi.org/10.3390/s140303861.
(Continued)

*Primary Examiner* — Jacques M Saint Surin
(74) *Attorney, Agent, or Firm* — Philip E. Levy; Eckert Seamans Cherin & Mellott, LLC

(57) ABSTRACT

A load cell apparatus includes a base member, a cap member, a number of first members provided between the base member and the cap member and forming at least a portion of a support wall of the load cell apparatus, and a plurality of strain gauges directly coupled to the number of first members, the plurality of strain gauges being positioned to measure an axial load applied to the load cell in a direction extending from the cap member to the base member.

21 Claims, 5 Drawing Sheets

(51) Int. Cl.
*G01G 3/14* (2006.01)
*G01G 19/44* (2006.01)
*G01L 1/22* (2006.01)

(52) U.S. Cl.
CPC ............... *G01G 3/14* (2013.01); *G01G 19/44* (2013.01); *G01L 1/2231* (2013.01); *A61B 2562/0252* (2013.01); *A61B 2562/0261* (2013.01)

(58) Field of Classification Search
CPC .. A61B 2562/0261; G01G 3/14; G01G 19/44; G01L 22/31; G01L 1/2218
USPC .......................................................... 177/211
See application file for complete search history.

(56) References Cited

U.S. PATENT DOCUMENTS

| | | | |
|---|---|---|---|
| 4,685,526 A | 8/1987 | Holm | |
| 5,092,163 A | 3/1992 | Young | |
| 5,313,023 A | 5/1994 | Johnson | |
| 5,393,938 A * | 2/1995 | Bumbalough | G01G 19/445 |
| | | | 177/144 |
| 5,823,278 A * | 10/1998 | Geringer | G01G 19/52 |
| | | | 177/144 |
| 5,969,268 A | 10/1999 | Sommerfeld et al. | |
| 7,178,391 B2 * | 2/2007 | Casper | E21B 49/00 |
| | | | 73/152.05 |
| 7,335,839 B2 * | 2/2008 | Metz | G01G 19/445 |
| | | | 177/144 |
| 2002/0157477 A1 * | 10/2002 | Hanson | G01L 1/162 |
| | | | 73/788 |
| 2006/0129047 A1 | 5/2006 | Ruotoistenmaki | |
| 2013/0014595 A1 | 1/2013 | Huizinga et al. | |

FOREIGN PATENT DOCUMENTS

| | | | | |
|---|---|---|---|---|
| WO | WO-2016116738 A1 * | 7/2016 | ............. | A61B 5/225 |
| WO | WO-2019140148 A1 * | 7/2019 | ............ | A61B 5/1036 |

OTHER PUBLICATIONS

Mhatre, A., Duvall, J., Ding, D., Cooper, R., & Pearlman, J. (2016). Design and focus group evaluation of a bed-integrated weight measurement system for wheelchair users. Assistive Technology. doi:10.1080/10400435.2016.1140690.

* cited by examiner

AXIAL LOAD CELL

CROSS-REFERENCE TO RELATED APPLICATIONS

This application is a U.S. National Stage Application under 35 U.S.C. § 371 of PCT International Application No. PCT/US2019/013129, filed on Jan. 11, 2019, entitled "AXIAL LOAD CELL" which claims priority under 35 U.S.C. § 119(e) from U.S. Provisional Patent Application No. 62/616,619, filed on Jan. 12, 2018, the contents of which are incorporated herein by reference.

GOVERNMENT CONTRACT

This invention was made with government support under grant #IIP1619990 awarded by the National Science Foundation (NSF). The government has certain rights in the invention.

BACKGROUND OF THE INVENTION

1. Field of the Invention

The present invention relates to load cells, and, in particular, a plastic axial load cell that may be used in a bed integrated weight measurement system or for wheelchair users.

2. Description of the Related Art

It has been shown that populations who track their weight on a regular basis can better maintain a healthy weight and decrease incidences of obesity, defined as a body mass index over 30. Higher obesity rates correspond to higher rates of cardiovascular disease, other health complications, and decreased quality of life.

Conventional weight measurement tools pose a challenge to many wheelchair users and those with impaired lower extremity function. Wheelchair users currently require the use of weight measurement tools only found in select health care provider offices, such as a sling scale or a roll on scale. Because accurate weight measurement requires assistance or a trip to a location outside of the home, it is a challenge for wheelchair users to independently track their weight and respond accordingly.

Wheelchair users are at higher risk for these problems than the general population because both mobility impairment and difficulty tracking weight are compounding factors which pose a challenge to maintaining a healthy life style.

An example load cell assembly and furniture integrated monitoring system are described in PCT/US16/13989, owned by the assignee of concept disclosed herein, the disclosure of which is Incorporated herein by reference. The described load cell assembly comprises a puck shaped device that includes only a single cantilever beam load cell which may cause accuracy deficiencies when a load is off center. To correct for such a deficiency, multiple cantilever beam load cells may be positioned around the outside of the load cell assembly. Such a configuration, however, may prove to be too costly for certain applications.

There is thus room for improvement in the area of load cells.

SUMMARY OF THE INVENTION

A load cell apparatus is provided that includes a base member, a cap member, a number of first members provided between the base member and the cap member and forming at least a portion of a support wall of the load cell apparatus, and a plurality of strain gauges directly coupled to the number of first members, the plurality of strain gauges being positioned to measure an axial load applied to the load cell in a direction extending from the cap member to the base member.

DETAILED DESCRIPTION OF EXEMPLARY EMBODIMENTS

Figure 1:
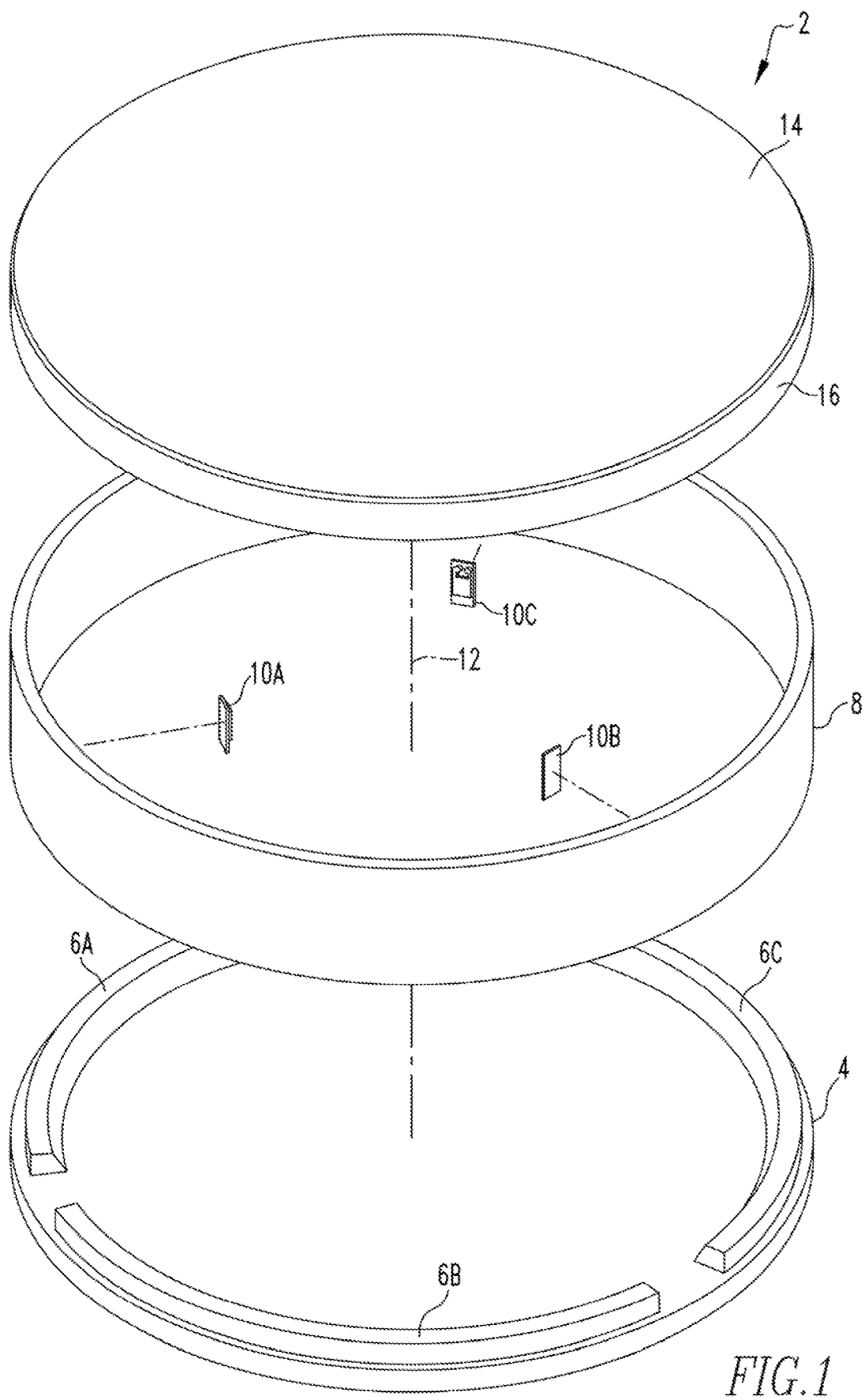
FIG. 1 is an exploded view and FIG. 2 is a schematic showing a load cell according to an exemplary embodiment of the disclosed concept.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs.

As used herein, "directly coupled" means that two elements are directly in contact with each other.

As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body.

As used herein, the statement that two or more parts or components "engage" one another shall mean that the parts exert a force against one another either directly or through one or more intermediate parts or components.

As used herein, the term "number" shall mean one or an integer greater than one (i.e., a plurality).

As used herein, the term "controller" shall mean a programmable analog and/or digital device (including an associated memory part or portion) that can store, retrieve, execute and process data (e.g., software routines and/or information used by such routines), including, without limitation, a field programmable gate array (FPGA), a complex programmable logic device (CPLD), a programmable system on a chip (PSOC), an application specific integrated circuit (ASIC), a microprocessor, a microcontroller, a programmable logic controller, or any other suitable processing device or apparatus. The memory portion can be any one or more of a variety of types of internal and/or external storage media such as, without limitation, RAM, ROM, EPROM(s), EEPROM(s), FLASH, and the like that provide a storage register, i.e., a non-transitory machine readable medium, for data and program code storage such as in the fashion of an internal storage area of a computer, and can be volatile memory or nonvolatile memory.

As used herein, the term "plastic" shall mean a material consisting of any of a wide range of synthetic or semi-synthetic organic compounds that may be shaped when soft, for example by applying heat and/or pressure, and then hardened, including many types of resins, resinoids, polymers, cellulose derivatives, casein materials, and proteins.

As used herein, the term "low modulus" material shall mean a Modulus of Elasticity/Young's Modulus (E) that is less than or equal to 10 GPa (E≤10 GPa), and shall include, without limitation, polymers, woods/wood products, foams, rubbers, and certain composites and porous ceramics.

As used herein, the term "substantially linear" shall mean having a coefficient of determination ($R^2$) of greater than or equal to 0.9.

As used herein, the term "strain gauge" shall mean a sensor device having a resistance that varies with applied force such that it converts force into a change in electrical resistance.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

The present invention will now be described, for purposes of explanation, in connection with numerous specific details in order to provide a thorough understanding of the subject invention. It will be evident, however, that the present invention can be practiced without these specific details without departing from the spirit and scope of this innovation.

Figure 2:
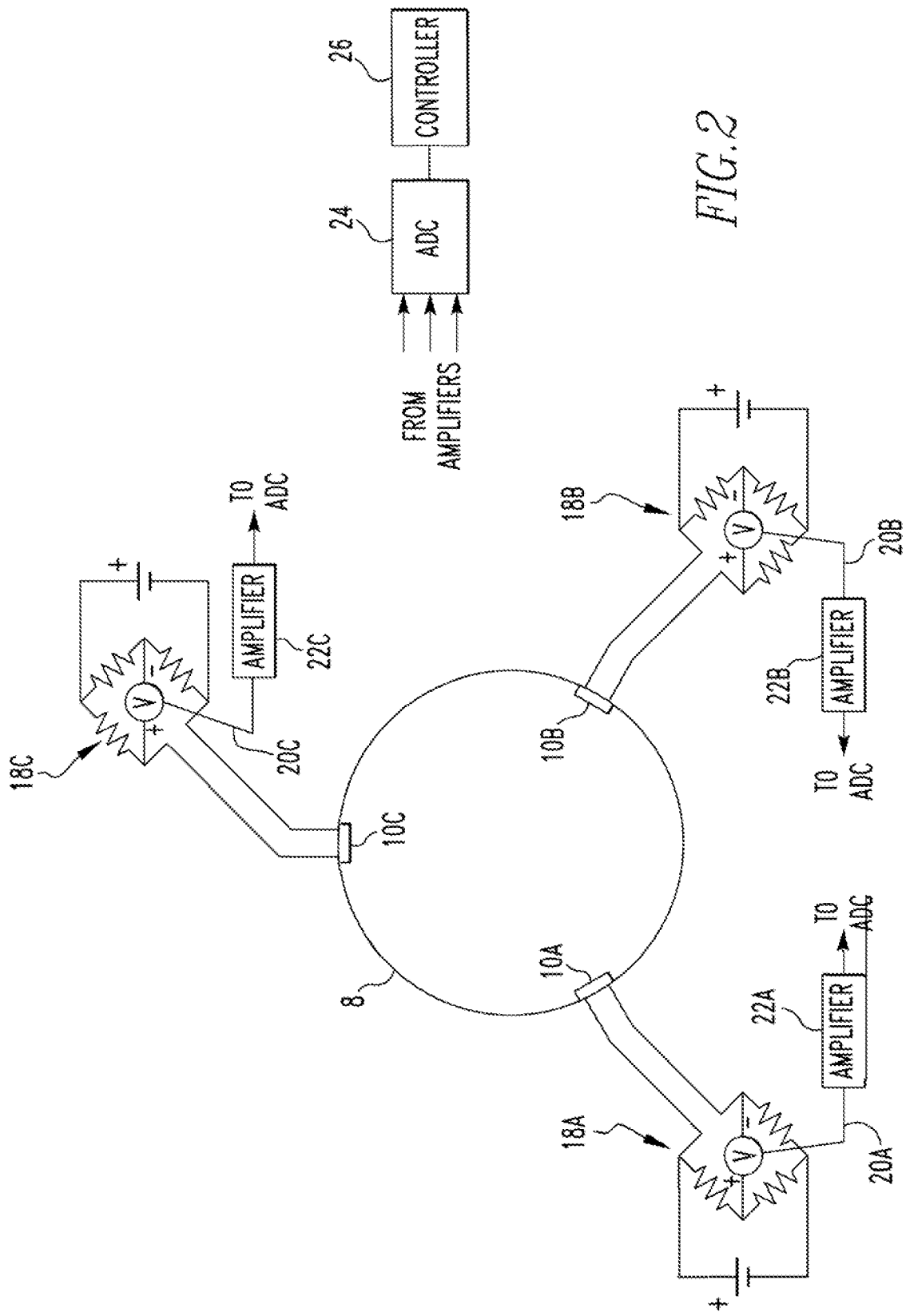

FIG. 1 is an exploded view and FIG. 2 is a schematic showing a load cell 2 according to an exemplary embodiment of the disclosed concept. Load cell 2 includes a base member 4 having spaced lip members 6A, 6B and 6C extending upwardly therefrom. In the exemplary embodiment, base member 4 is made from a plastic material, although it will be appreciated that other materials are also possible. Load cell to further includes a cylindrical ring member 8 made of a low modulus material, such as, without limitation, plastic (e.g., PVC). In addition, in the exemplary embodiment, ring member 8 is made of a material having a substantially linear stress strain curve. In particular exemplary embodiments, ring member 8 is made of a material having a coefficient of determination ($R^2$) of greater than or equal to 0.95 or greater than or equal to 0.98. Ring member 8 is structured to be received by base member 4 by extending around lip members 6A, 6B and 6C such that lip members 6A, 6B and 6C engage the inner surface of ring member 8. In the exemplary embodiment, ring member 8 is made from polyvinyl chloride (PVC), although other plastic materials may also be used. While ring member 8 is cylindrical in shape in the illustrated, exemplary embodiment, it will be appreciated that other geometric shapes are also contemplated within the scope of the disclosed concept.

A plurality of strain gauges 10 are directly coupled ring member 8. In the exemplary embodiment, load cell 2 includes three strain gauges 10, labeled 10A, 10B, and 10C, although it will be appreciated that this is not meant to be living in that more or less than three strain gauges 10 they also be used. In one example embodiment, strain gauges 10 are directly coupled to the inner surface of ring member 8 by a suitable means such as, without limitation, an adhesive. In an alternative example embodiment, strain gauges 10 are integrally molded with ring member 8. In the illustrated exemplary embodiment, strain gauges 10A, 10B, and 10C are spaced 120 degrees apart from one another around the periphery of ring member 8. In addition, in the illustrated exemplary embodiment, strain gauges 10A, 10B, and 10C are each centered along a height of ring member 8, with the height being measured in a direction parallel to a longitudinal axis 12 of load cell 2. In addition, each strain gauge 10A, 10B, and 10C is positioned to measure an axial load applied to the load cell 2 in a direction parallel to the longitudinal axis 12. A cap member 14 having an outer edge 16 is provided on top of ring member 8 such that the outer surface of ring member 8 gauges inner surface of outer age 16. In the non-limiting, exemplary embodiment, cap member 14 is made of a metal such as aluminum.

As seen in FIG. 2, each strain gauge 10A, 10B, and 10C is provided as part of an associated Wheatstone quarter bridge configuration 18, labeled 18A, 18B, and 18C in FIG. 2. In addition, a voltage output 20, labeled 20A, 20B, and 20C, is provided to an amplifier 22 associated with each strain gauge 10A, 10B, and 10C (amplifier 22 are labeled 22A, 22B, and 22C in FIG. 2). The illustrated exemplary embodiment, the amplifier outputs are provided to an analog-to-digital converter 24 coupled to a controller 26. Thus, in the illustrated exemplary embodiment, an appropriate gain constant is determined for each strain gauge 10A, 10B, and 10C, and the outputs of amplifiers 22A, 22B, and 22C may be averaged to appropriately cancel bending loads. Although shown outside of ring member 8 in FIG. 2, the electronic components just described may be placed inside ring member 8 such that ring member 8 serves as both a load measuring device and a housing.

In operation, when an axial load is applied to member 14, the force from that load is transferred to ring 8. When such force is applied, each strain gauge assembly including strain gauges 10A, 10B, and 10C, Wheatstone quarter bridge configurations 18A, 18B, and 18C, amplifiers 22A, 22B, and 22C will generate signals indicative thereof that are provided controller 26. The information indicative of load applied to load cell to me then be used by controller 26 to determine various items of information such as, without limitation, weight.

Figure 3:
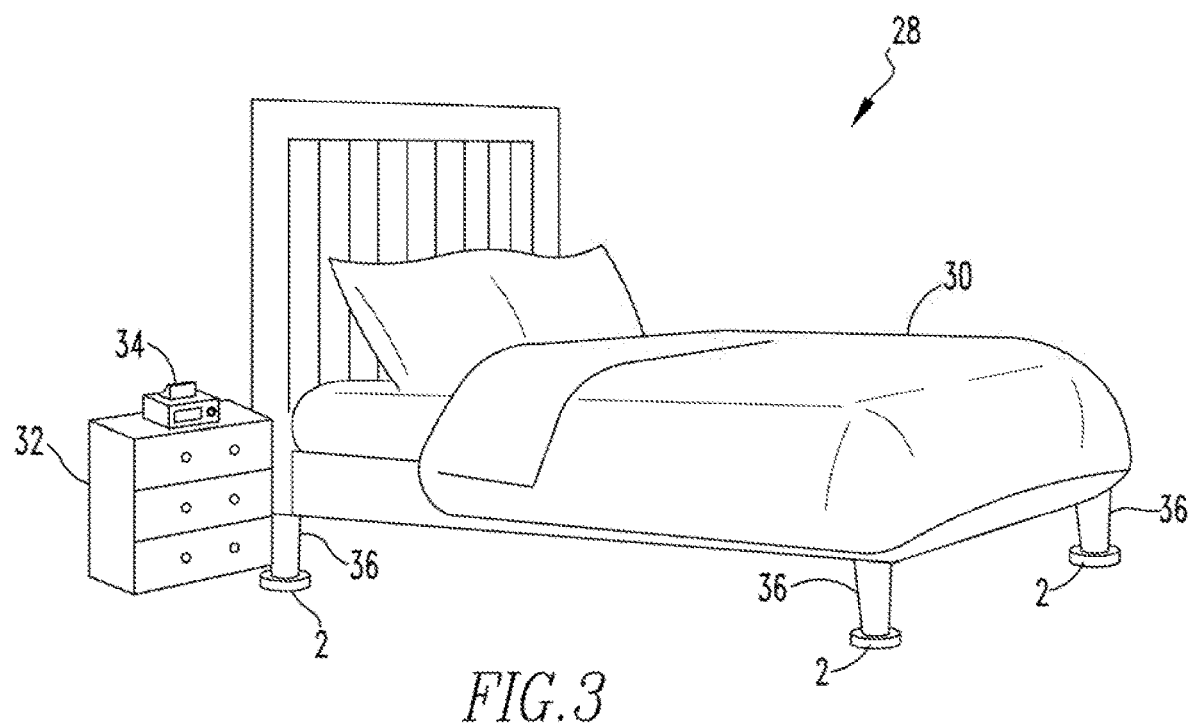
FIG. 3 is a schematic diagram of an exemplary bed-integrated monitoring system for in-home use employing the disclosed concept.

Analog-to-digital converter 24 and/or controller 26 may be local to load cell 2 or maybe located remotely from load cell 2, and data may be transferred from load cell to two those components in a wired or wireless fashion. For example, FIG. 3 is a schematic diagram of an exemplary bed-integrated monitoring system 28 for in-home use employing the disclosed concept that may be used for measuring and monitoring the weight of one or more individuals, such as one or more wheelchair users. As seen in FIG. 3, in the exemplary embodiment, monitoring system 28 is integrated in a home environment, such as a bedroom, that includes a bed 30 and a nightstand 32. Monitoring system 28 includes a plurality of (e.g., four) load cells 2 that are operatively coupled to a control unit 34 including analog-to-digital converter 24 and controller 26. In the illustrated embodiment, each load cell 2 is positioned beneath a respective one of the legs 36 of bed 30, and control unit 34 is positioned on nightstand 32. Each load cell 2 is structured to measure the magnitude of a force that is being applied axially thereto by the respective leg 36 and to generate a signal indicative of that force as described herein. In addition, each load cell 2 is in electronic communication with control unit 34. In the exemplary embodiment, each load cell 2 is wirelessly connected to control unit 34 to provide such electronic communication (e.g., by having an onboard power source and wireless communications module such as a Bluetooth® module), although it will be understood that such electronic communication may also be provided via a wired connection. Control unit 34 is structured to receive each of the force signals from the load cells 2, which together are indicative of the weight present on bed 30, and to determine and display weight information relating to the weight of one or more users of bed 30. In the non-limiting exemplary embodiment, controller 26 in control unit 34 implements an algorithm that sums the weight data from each load cell 2 and based thereon determines and displays the current weight of a user resting on bed 34. The weight data may be sampled periodically, e.g. every second, and controller 26 of control unit 34 has the capacity to log weight data for a period of time, such as one year.

Figure 4:
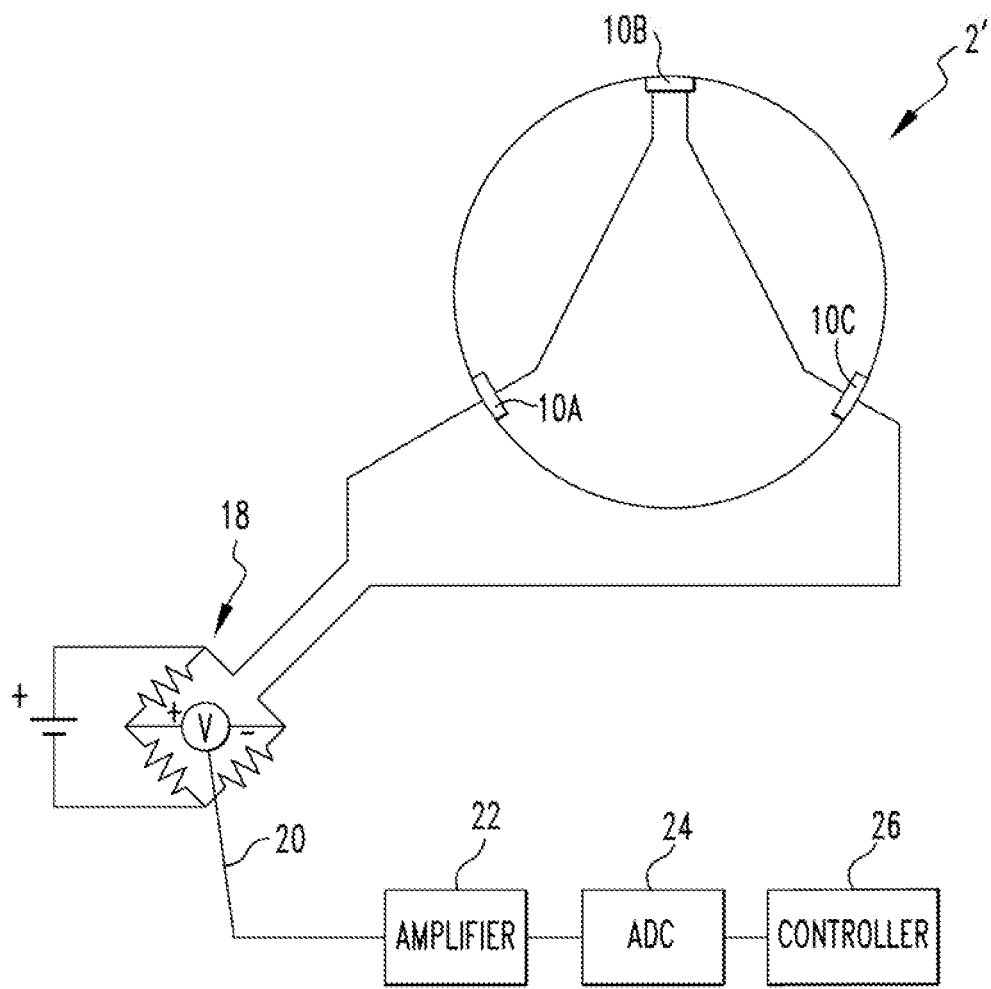
FIG. 4 is a schematic diagram showing an alternative load cell according to an alternative exemplary embodiment of the disclosed concept.

FIG. 4 is a schematic diagram showing an alternative load cell, labeled 2', according to an alternative exemplary embodiment of the disclosed concept that may be used as a substitute for load cell 2 in the embodiments described herein. Load cell 2' is similar to load cell 2, and like components are labeled with like reference numerals. However, in load cell 2', strain gauges 10A, 10B, and 10C are connected in series and form part of a single Wheatstone bridge configuration 18. The series connection of strain gauges 10A, 10B, and 10C will "average" the strain and cancel out any bending moments. While this embodiment incorrectly assumes that strain gauges 10A, 10B, and 10C will have equal strains and equal gauge factors, in practice it is likely that the values will be close enough such that measurements not be adversely affected.

Figure 5:
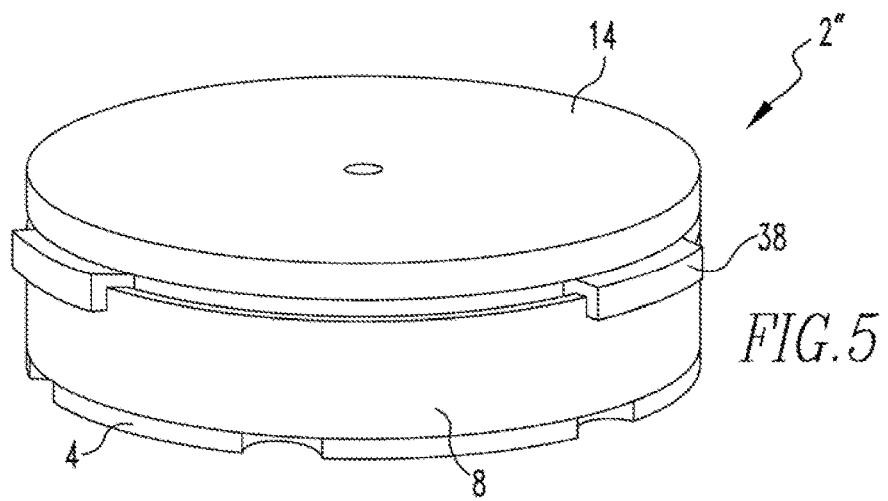
FIGS. 5-9 are schematic diagrams showing an alternative load cell according to another alternative exemplary embodiment of the disclosed concept.
Figure 6:
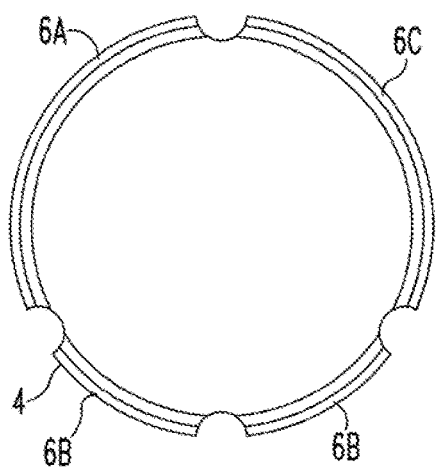
Figure 7:
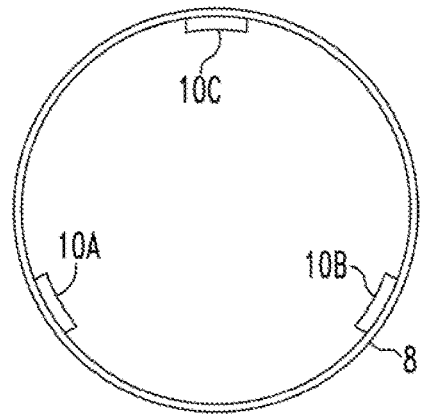
Figure 8:
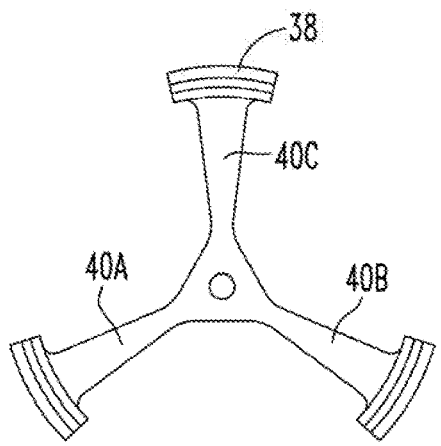
Figure 9:
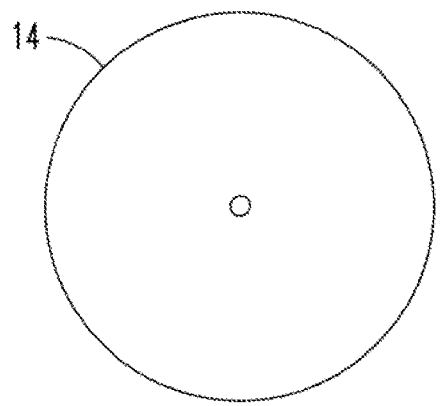

FIGS. 5-9 are schematic diagrams showing an alternative load cell, labeled 2'', according to another alternative exemplary of the disclosed concept that may be used as a substitute for load cell 2 in the embodiments described herein. Load cell 2'' is similar to load cell 2, and like components are labeled with like reference numerals. However, load cell 2'' further includes a plastic spoked lid member 38 provided between cap member 14 ring member 8. Spoked lid member 38 includes a plurality of spokes 40, labeled 40A, 40B, and 40C in the illustrated example. As seen in FIG. 5, the end portion of each of the spokes 40A, 40B, and 40C is positioned directly above a corresponding one of strain gauges 10A, 10B, and 10C.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A load cell apparatus, comprising:
   a base member;
   a cap member;
   a number of first members provided between the base member and the cap member and forming at least a portion of a support wall of the load cell apparatus, wherein each of the number of first members is made of a material having a substantially linear stress-strain curve; and
   a plurality of strain gauges directly coupled to the number of first members, the plurality of strain gauges being positioned to measure an axial load applied to the load cell in a direction extending from the cap member to the base member.

2. The load cell apparatus according to claim 1, wherein the number of first members comprises a cylindrical ring member.

3. The load cell apparatus according to claim 1, wherein each of the number of first members is made of a low modulus material.

4. The load cell apparatus according to claim 3, wherein the low modulus material is plastic.

5. The load cell apparatus according to claim 1, wherein the number of first members comprises a plurality of post members spaced around a periphery of the load cell apparatus.

6. The load cell apparatus according to claim 5, wherein the post members are provided around a ring member provided between the base member and the cap member.

7. The load cell apparatus according to claim 1, wherein the plurality of strain gauges is directly coupled to an exterior surface of the number of first members.

8. The load cell apparatus according to claim 1, wherein the plurality of strain gauges is integrally molded with the number of first members.

9. The load cell apparatus according to claim 1, wherein each of the plurality of strain gauges is a linear strain gauge.

10. The load cell apparatus according to claim 1, wherein the plurality of strain gauges are evenly spaced around a periphery of the load cell apparatus.

11. The load cell apparatus according to claim 10, wherein the plurality of strain gauges comprises three strain gauges spaced 120 degrees apart from one another around the periphery of the load cell apparatus.

12. The load cell apparatus according to claim 1, wherein each of the strain gauges is centered along a height of the number of first members.

13. The load cell apparatus according to claim 1, wherein the number of first members is made of polyvinyl chloride.

14. The load cell apparatus according to claim 1, further comprising a plurality of Wheatstone bridge circuits, wherein each of the strain gauges is provided as part of a respective one of the Wheatstone bridge circuits.

15. The load cell apparatus according to claim 1, further comprising a Wheatstone bridge circuit, wherein the plurality of strain gauges are connected in series and are provided as part of the Wheatstone bridge circuit.

16. The load cell apparatus according to claim 1, further comprising a number of amplifiers coupled to the plurality of strain gauges.

17. A system for measuring a weight of an individual including one or more load cell apparatuses according to claim 1.

18. The load cell apparatus according to claim 1, wherein each of the number of first members is made of a material having a coefficient of determination ($R^2$) of greater than or equal to 0.95.

19. The load cell apparatus according to claim 1, wherein each of the number of first members is made of a material having a coefficient of determination ($R^2$) of greater than or equal to 0.98.

20. A load cell apparatus, comprising:
   a base member;
   a cap member;
   a number of first members provided between the base member and the cap member and forming at least a portion of a support wall of the load cell apparatus;
   a plurality of strain gauges directly coupled to the number of first members; the plurality of strain gauges being positioned to measure an axial load applied to the load cell in a direction extending from the cap member to the base member; and
   a lid member provided between the cap member and the number of first members, wherein the lid member includes a plurality of spokes, wherein an end portion of each of the spokes is positioned directly above a corresponding one of the plurality of strain gauges.

21. The load cell apparatus according to claim 20, wherein each of the number of first members is made of a material having a substantially linear stress-strain curve.

* * * * *